US012767913B2

(12) United States Patent
Park et al.

(10) Patent No.: US 12,767,913 B2
(45) Date of Patent: Oct. 20, 2026

(54) HYBRID ASEPTIC CONNECTION SYSTEM AND ASEPTIC CONNECTION METHOD FOR ANTIBODY PHARMACEUTICAL MANUFACTURING PROCESS

(71) Applicant: PRESTIGE BIOLOGICS CO., LTD., Chungcheongbuk-do (KR)

(72) Inventors: Joo Yang Park, Seoul (KR); Ja Won Shin, Sejong (KR); Dae Yang Oh, Seoul (KR)

(73) Assignee: PRESTIGE BIOLOGICS CO., LTD., Cheongju-si (KR)

( * ) Notice: Subject to any disclaimer, the term of this patent is extended or adjusted under 35 U.S.C. 154(b) by 917 days.

(21) Appl. No.: 17/910,577

(22) PCT Filed: Mar. 8, 2021

(86) PCT No.: PCT/KR2021/002836
§ 371 (c)(1),
(2) Date: Sep. 9, 2022

(87) PCT Pub. No.: WO2021/194127
PCT Pub. Date: Sep. 30, 2021

(65) Prior Publication Data

US 2023/0167389 A1 Jun. 1, 2023

(30) Foreign Application Priority Data

Mar. 23, 2020 (KR) ........................ 10-2020-0035265

(51) Int. Cl.
*C12M 1/00* (2006.01)
*C12M 1/34* (2006.01)

(52) U.S. Cl.
CPC ............ *C12M 21/02* (2013.01); *C12M 23/28* (2013.01); *C12M 41/44* (2013.01); *C12M 45/22* (2013.01)

(58) Field of Classification Search
CPC ...... C12M 21/02; C12M 23/28; C12M 41/44; C12M 45/22; C12M 23/14; C12M 23/40; C12M 23/46; C12M 37/00; C12M 39/00
See application file for complete search history.

(56) References Cited

U.S. PATENT DOCUMENTS

2005/0239198 A1* 10/2005 Kunas .................... C12M 23/26 435/297.1
2009/0053800 A1 2/2009 Friend et al.
(Continued)

FOREIGN PATENT DOCUMENTS

CN 208191734 U 12/2018
KR 10-0767569 B1 10/2007
(Continued)

OTHER PUBLICATIONS

Office Action from corresponding Korean Patent Application No. 10-2020-0035265, dated Aug. 23, 2021.
(Continued)

*Primary Examiner* — William H. Beisner
*Assistant Examiner* — Danielle B Henkel
(74) *Attorney, Agent, or Firm* — Dinsmore & Shohl LLP; Yongsok Choi, Esq.

(57) ABSTRACT

The present invention relates to a hybrid aseptic connection system and aseptic connection method for manufacturing an antibody pharmaceutical. In a hybrid system employing a medium storage tank made of a SS material and a bioreactor made of an SU disposable tube, to ensure a completely aseptic connection between the medium storage tank and the bioreactor, the completely aseptic connection between the medium storage tank and the bioreactor may be made by interconnection of the SU disposable tube through a welding process and the advantages of both the SS system and the SU system may be obtained at the same time. As a discharge line, an SU disposable tube and a steam trap tube are formed
(Continued)

in a “Y” shape, the flowability in a medium transfer line may be improved and thus it is possible to prevent impurities such as a condensate from remaining in the medium transfer line.

3 Claims, 3 Drawing Sheets

(56) References Cited

U.S. PATENT DOCUMENTS

| | | | | |
|---|---|---|---|---|
| 2009/0311776 | A1* | 12/2009 | Kelly, Jr. | C12M 23/38 435/289.1 |
| 2010/0209966 | A1 | 8/2010 | Everett | |
| 2016/0297152 | A1 | 10/2016 | Maggiore | |
| 2016/0327960 | A1 | 11/2016 | Li | |
| 2017/0335268 | A1* | 11/2017 | Maggiore | B33Y 10/00 |
| 2017/0349874 | A1 | 12/2017 | Jaques et al. | |
| 2018/0229241 | A1* | 8/2018 | Bishop | C12M 29/26 |
| 2019/0031998 | A1* | 1/2019 | Valonen | C12M 1/02 |

FOREIGN PATENT DOCUMENTS

| | | | |
|---|---|---|---|
| KR | 10-2017-0093866 | A | 8/2017 |
| KR | 10-2018-0047404 | A | 5/2018 |
| KR | 10-2000200 | B1 | 7/2019 |
| WO | 2018148346 | A1 | 8/2018 |

OTHER PUBLICATIONS

Gronemeyer, P., et al.; “Trends in Upstream and Downstream Process Development for Antibody Manufacturing”, *Bioengineering* 2014, 1, 188-212; doi:10.3390/bioengineering1040188.

Larroche, C., et al.; “Current Developments in Biotechnology and Bioengineering Bioprocesses”, Bioreactors and Controls, Elsevier, 2017.

International Search Report from corresponding PCT Application No. PCT/KR2021/002836, dated Jun. 23, 2021.

Merck KGaA [online]Mobius 3L Single-use Bioreactor, Internet Archive: Wayback Machine ] https://web.archive.org/web/20181021032345/http://www.merckmillipore.com:80/JP/en/product/Mobius-3L-Single-use-Bioreactor, MM_NF-C84539.

Extended European Search Report for EP21776172.5 issued Sep. 24, 2025.

* cited by examiner

HYBRID ASEPTIC CONNECTION SYSTEM AND ASEPTIC CONNECTION METHOD FOR ANTIBODY PHARMACEUTICAL MANUFACTURING PROCESS

CROSS-REFERENCE TO RELATED APPLICATIONS

This application is a National Phase application of PCT Application No. PCT/KR2021/002836, filed on 8 Mar. 2021, which claims priority to Korean Patent Application No. 10-2020-0035265, filed on 23 Mar. 2020. The entire disclosures of the applications identified in this paragraph are incorporated herein by reference.

TECHNICAL FIELD

The present invention relates to a hybrid aseptic connection system and aseptic connection method for a process of manufacturing an antibody pharmaceutical.

BACKGROUND ART

Biopharmaceuticals can be broadly classified into new biologics, improved biopharmaceuticals (biobetters) and biosimilars, and compared with chemically synthesized pharmaceuticals, have fewer side effects and less preclinical data required in research and development, and are easier to predict product efficacy and safety and due to the relatively high probability of clinical success, active development of technology is progressing worldwide.

The process of manufacturing biopharmaceuticals consists of initial candidate material and cell line development, a culture process (upstream processing (USP)), a purification process (downstream processing (DSP)), and a fill and finish process, and particularly, in the case of biosimilar product production, processing optimization in the culture process (USP) and purification process (DSP) is directly related to cost competitiveness, so interest in optimizing the process of manufacturing biosimilars with low cost, high purity and high yield is growing.

In this process, the culture process (USP) corresponds to the process of continuously increasing the number of cells through cell division for approximately 6 weeks from the initial flask stage of less than 1 liter to the final production bioreactor stage of 15,000 L or more, after thawing the cell line, and culture methods that can be used herein include batch culture, fed-batch culture, continuous culture, and perfusion culture and the like.

Meanwhile, the purification process (DSP)is the process of extracting a protein to be used as a pharmaceutical with high purity and high efficiency from the culture in which cells and cell debris are mixed through the manipulation and use of various types of chromatographs and filters, and during the purification process (DSP), column purification, virus removal and ultra/diafiltration are performed through the use of a chromatograph and filters.

Meanwhile, components and systems used in the USP and DSP are divided into stainless steel (SS) and single-use (SU) using disposable bags or tubes in terms of material, and among these, although the SS process system including device components made of SS has advantages of easy implementation on a relatively large scale, low operation cost and easy automation, the initial installation cost is high, it is vulnerable to contamination and prone to the downstream bottleneck phenomenon occurring in the DSP, caused by the implementation of a large-sized bioreactor.

The SU process system, which has recently been introduced, uses disposable bags or tubes with a volume of 0.1 to 2,000 L as device components, and compared to the SS process system, has advantages of relatively low cost for initial installation and being relatively resistant to contamination because a corresponding part can be replaced upon contamination. However, scale-up limitations, continuous operation costs caused by frequent bag replacement and the input of a lot of labor during equipment replacement are pointed out as disadvantages.

In the field of biopharma today, there are more and more companies serving as contract manufacturing organizations (CMOs) for drugs for clinical trials and commercial use, and furthermore, improvement in one-stop service from cell line development and related process development, scale-up to commercial production is also made.

Meanwhile, in the culture process for producing a target protein, a medium which is a nutrient mixture for cell culture or microbial culture is used, and a medium transferred from a medium preparation tank to a medium storage tank is also transferred to a bioreactor. Here, the medium storage tank that supplies the medium is formed of a stainless steel (SS) material, and the bioreactor that receives the medium may be formed of a single-use (SU) disposable bag material. In this hybrid system, the medium storage tank and the bioreactor have to be connected with complete sterility, and when sterility is not ensured, it may be difficult to produce a desired antibody pharmaceutical due to medium contamination or the introduction of a contaminant.

DISCLOSURE

Technical Problem

In view of the above problems, the present invention is directed to providing a hybrid aseptic connection system and aseptic connection method for a process of manufacturing an antibody pharmaceutical. In a hybrid system employing a medium storage tank made of a SS material and a bioreactor made of an SU disposable bag, to ensure a completely aseptic connection between the medium storage tank and the bioreactor, the completely aseptic connection between the medium storage tank and the bioreactor may be made by interconnection of an SU disposable tube through a welding process and the advantages of both the SS system and the SU system may be obtained at the same time. As a discharge line, an SU disposable tube and a steam trap tube are formed in a “Y” shape, the flowability in a medium transfer line may be improved and thus it is possible to prevent impurities such as a condensate from remaining in the medium transfer line, thereby preventing medium contamination in advance.

In addition, technical problems to be solved in the present invention are not limited to the above-described technical problems, and other problems which are not described herein will be fully understood by those of ordinary skill in the art from the following descriptions.

Technical Solution

The specification provides a hybrid aseptic connection system for a process of manufacturing an antibody pharmaceutical, which includes: a medium storage tank made of a stainless steel material, which stores a medium received from a media preparation tank; a bioreactor made of a single-use (SU) disposable bag, which includes a stirring device, receives the medium from the medium storage tank and increases the number of cells through cell division; and a medium transfer line configured to introduce a medium stream discharged from the medium storage tank to the bioreactor, wherein the medium transfer line includes a fastening part formed at the end of a discharge line provided at one end of the medium storage tank; an SU disposable tube connected with the discharge line using the fastening part at one end and connected with the bioreactor at the other end; and a vent filter provided on the tube to prevent the expansion and contraction of the tube by a steam sterilization process.

In addition, in the specification, the discharge line and the SU disposable tube are connected with each other while being inclined at predetermined angles, respectively.

In addition, in the specification, the hybrid aseptic connection system further includes a steam trap tube which is formed to branch from the fastening part and include a pinch clamp.

In addition, in the specification, the discharge line, the SU disposable tube and the steam trap tube are formed in an "Y" shape.

In addition, in the specification, the SU disposable tube is formed by welding a tube pre-connected with the fastening part and a tube included in the bioreactor.

In addition, in the specification, the aseptic connection system is applied to provide a medium for a process of manufacturing one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin, and interferon gamma-1b.

In addition, the specification provides an aseptic connection method in a hybrid system for a process of manufacturing an antibody pharmaceutical, which includes: (a) after transferring a medium from a medium storage tank to a bioreactor, removing an SU disposable tube that has been used; (b) connecting a new disposable tube to a fastening part first, cleaning the medium storage tank, the discharge line and the disposable tube in place, drying the resulting product using clean and oil-free air (COA), and then sterilizing the dried product with high-temperature steam; and (c) aseptically connecting, after the sterilization, the disposable tube with a tube included in a newly-prepared bioreactor made of a single-use (SU) disposable bag through a welding process.

In addition, the specification provides an aseptic connection method in a hybrid system for a process of manufacturing an antibody pharmaceutical, which includes: (a) after transferring a medium from a medium storage tank to a bioreactor, removing an SU disposable tube that has been used; (b) preparing a new disposable tube having a diaphragm valve at one end and a vent filter at the other end, cleaning the tube in place, drying it using clean and oil-free air (COA) and then sterilizing it with high temperature steam; and (c) connecting, after the sterilization, the end at which the diaphragm valve of the disposable tube is placed with a discharge line of a medium storage tank via a fastening part, and aseptically connecting the end at which the vent filter is included with a tube included in a newly prepared bioreactor made of an SU disposable bag through a welding process.

Advantageous Effects

According to an aseptic connection system and aseptic connection method according to the present invention, in a hybrid system employing a medium storage tank made of an SS material and a bioreactor made of an SU disposable bag, a completely aseptic connection between the medium storage tank and the bioreactor can be secured and the advantages of each of the SS system and the SU system can be obtained at the same time by interconnection of the SU disposable tube through a welding process.

In addition, in the aseptic connection system according to the present invention, by forming a discharge line, an SU disposable tube and a steam trap tube in a "Y" shape, the flowability in a medium transfer line can be improved, thereby preventing impurities such as a condensate from remaining in the medium transfer line and thus preventing medium contamination in advance.

Further, the aseptic connection system and aseptic connection method according to the present invention can exclude complicated piping caused by the single use of a conventional SU system, and due to the advantages of resistance to contamination compared to the single use of a conventional SS system, can secure the economic feasibility and efficiency of the process.

MODES OF THE INVENTION

Figure 1:
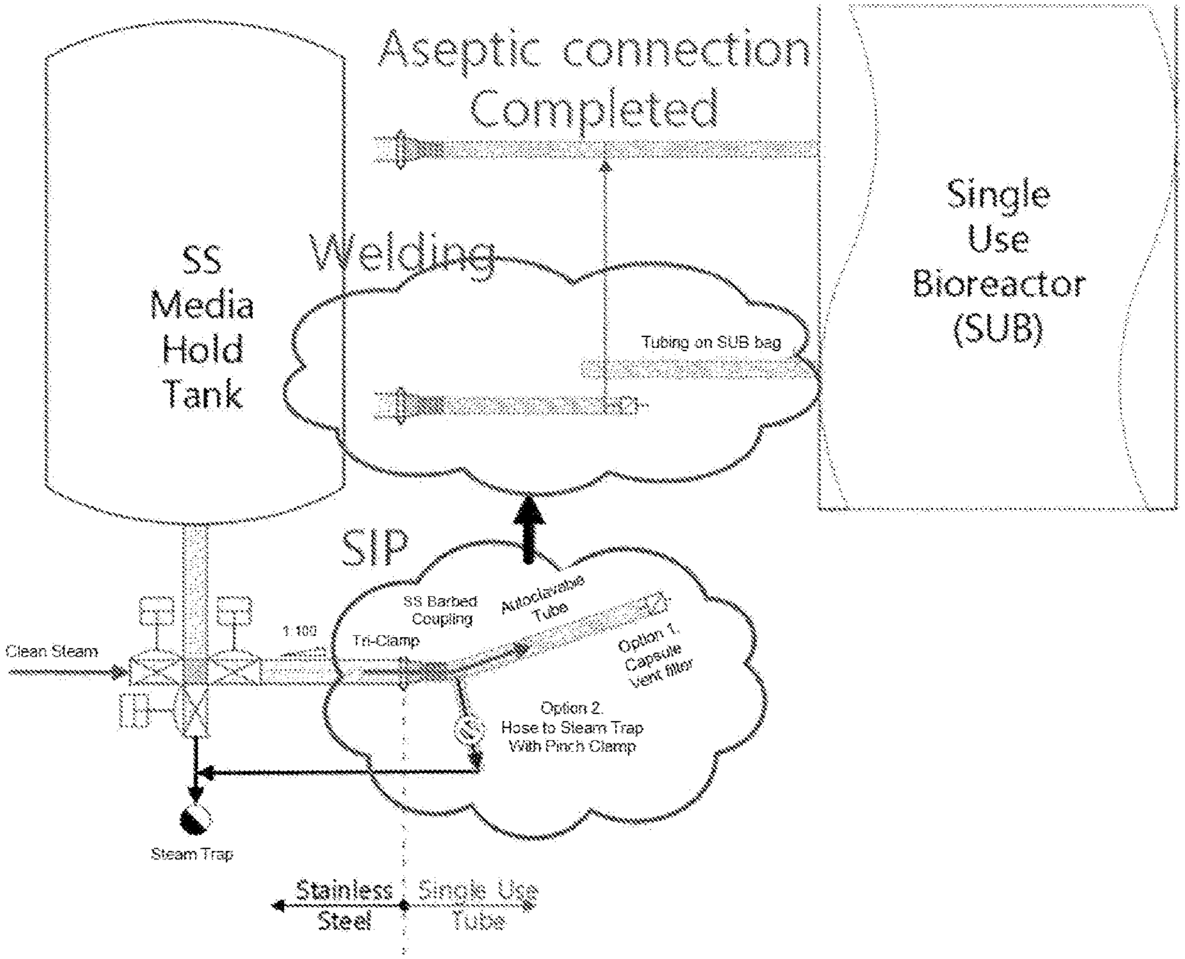
FIG. 1 schematically shows an aseptic connection system in which a connection securing complete sterility between a medium storage tank made of an SS material and a bioreactor made of an SU disposable bag through a welding process according to one embodiment of the present invention.

The terms used in the specification are used only to describe specific examples, not to limit the present invention. Singular expressions include plural expressions unless clearly indicated otherwise in the context. It should be understood that the term "comprise," "include," or "have" used herein is for indicating the presence of implemented characteristics, numbers, steps, elements or a combination thereof, and does not preclude the possibility of the presence or addition of one or more other characteristics, numbers, steps, elements or a combination thereof.

In addition, in the present invention, when a layer or element is referred to as being formed "on" or "over" each layer or element, it is meant that each layer or element is formed directly on each layer or element, or another layer or element is formed on each layer, or that another layer or element may additionally be formed between layers, on an object, or a substrate.

The present invention may have various modifications and various examples, and thus specific examples are illustrated in the drawings and described in detail in the detailed description. However, it should be understood that the present invention is not limited to specific embodiments, and includes all modifications, equivalents or alternatives within the spirit and technical scope of the present invention.

Hereinafter, a hybrid aseptic connection system and aseptic connection method for a process of manufacturing an antibody pharmaceutical according to an exemplary embodiment of the present invention will be described in further detail.

Hybrid Aseptic Connection System for Process of Manufacturing Antibody Pharmaceutical A hybrid aseptic connection system for a process of manufacturing an antibody pharmaceutical according to one embodiment of the present invention may include a medium storage tank made of a stainless steel material, which stores a medium received from a media preparation tank; a bioreactor made of a single-use (SU) disposable bag, which includes a stirring device, receives the medium from the medium storage tank and increases the number of cells through cell division; and a medium transfer line configured to introduce a medium stream discharged from the medium storage tank to the bioreactor, wherein the medium transfer line includes a fastening part formed at the end of a discharge line provided at one end of the medium storage tank; an SU disposable tube connected with the discharge line using the fastening part at one end and connected with the bioreactor at the other end; and a vent filter provided on the tube to prevent the expansion and contraction of the tube by a steam sterilization process.

In further detail, the process of manufacturing an antibody pharmaceutical consists of initial candidate material and cell line development, a culture process (upstream processing (USP)), a purification process (downstream processing (DSP)), and a fill and finish process.

Among these processes, the culture process (USP) corresponds to the process of continuously increasing the number of cells through cell division for approximately 6 weeks from the initial flask stage of less than 1 liter to the final production bioreactor stage of 15,000 L or more, after thawing the cell line.

The cultivation unit according to the present invention is a set of components for the culture process (USP), which may include a medium preparation tank for preparing a medium in advance, a medium storage tank for receiving the media from the medium preparation tank and storing the medium, a feed line through which a feed stream including thawed cells and a culture medium is introduced to a bioreactor, one or more bioreactors including a stirring system, which receive the thawed cells and the medium from the feed stream and increase the number of cells through cell division, and a discharge line which discharges the medium containing the cells cultured in the bioreactor as an effluent stream.

Meanwhile, the components and systems used in the USP and DSP are divided into stainless steel (SS) and single-use (SU) using disposable bags or tubes in terms of material, and among these, although the SS process system including device components made of SS has advantages of easy implementation on a relatively large scale, low operation cost and easy automation, the initial installation cost is high, it is vulnerable to contamination and prone to the downstream bottleneck phenomenon occurring in the DSP, caused by the implementation of a large-sized bioreactor.

The SU process system, which has recently been introduced, uses disposable bags or tubes with a volume of 0.1 to 2,000 L as device components, and compared to the SS process system, has advantages of relatively low cost for initial installation and being relatively resistant to contamination because a corresponding part can be replaced upon contamination. However, scale-up limitations, continuous operation costs caused by frequent bag replacement and the input of a lot of labor during equipment replacement are pointed out as disadvantages.

The present inventors confirmed that, to obtain the advantages of both the SS system and the SU system, in a culture process (USP), in the hybrid system in which the medium storage tank providing a medium is formed of a stainless steel (SS) material and the bioreactor receiving the medium is formed of a single-use (SU) disposable bag, in order to secure a completely aseptic connection between the medium storage tank and the bioreactor, by interconnection of the SU disposable tube through a welding process, the completely aseptic connection between the medium storage tank and the bioreactor may be secured and the advantages of the SS system and the SU system may be obtained at the same time, and as the medium transfer line includes a discharge line, a fastening part, an SU disposable tube, a vent filter and a steam trap tube, which are formed in a "Y" shape, impurities such as condensate may be prevented from remaining in the medium transfer line and thus medium contamination is prevented in advance. Thus, the present invention was completed.

Specifically, according to one embodiment of the present invention, the medium transfer line may include a fastening part formed at the end of a discharge line provided at one end of the medium storage tank; an SU disposable tube connected with the discharge line using the fastening part at one end and connected with the bioreactor at the other end; and a vent filter provided on the tube to prevent the expansion and contraction of the tube by a steam sterilization process, wherein the discharge line and the SU disposable tube are connected with each other while being inclined at predetermined angles, respectively.

In one example, each of the discharge line and the SU disposable tube is included to form an acute angle based on the ground and may be connected to each other in a "V" shape through the fastening part.

Meanwhile, the hybrid aseptic connection system according to one embodiment of the present invention may further include a steam trap tube branched from the fastening part and including a pinch clamp, and here, the discharge line, SU disposable tube and steam trap tube may be formed in a "Y" shape.

Figure 2:
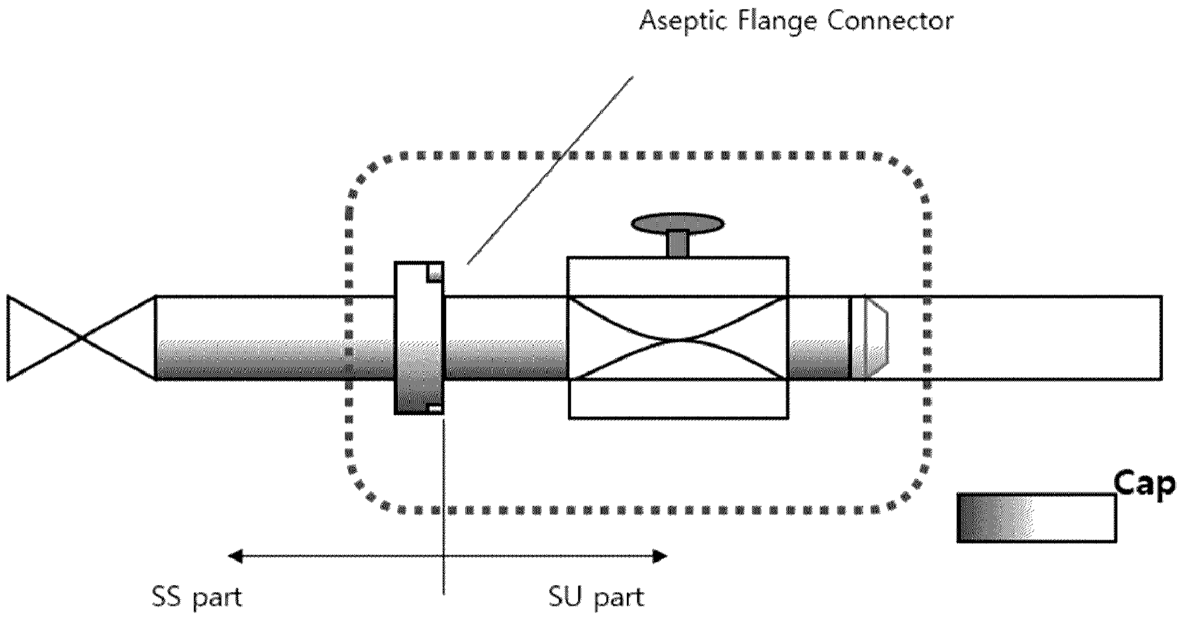
FIG. 2 shows a fastening part of an aseptic connection system according to one embodiment of the present invention in detail.
Figure 3:
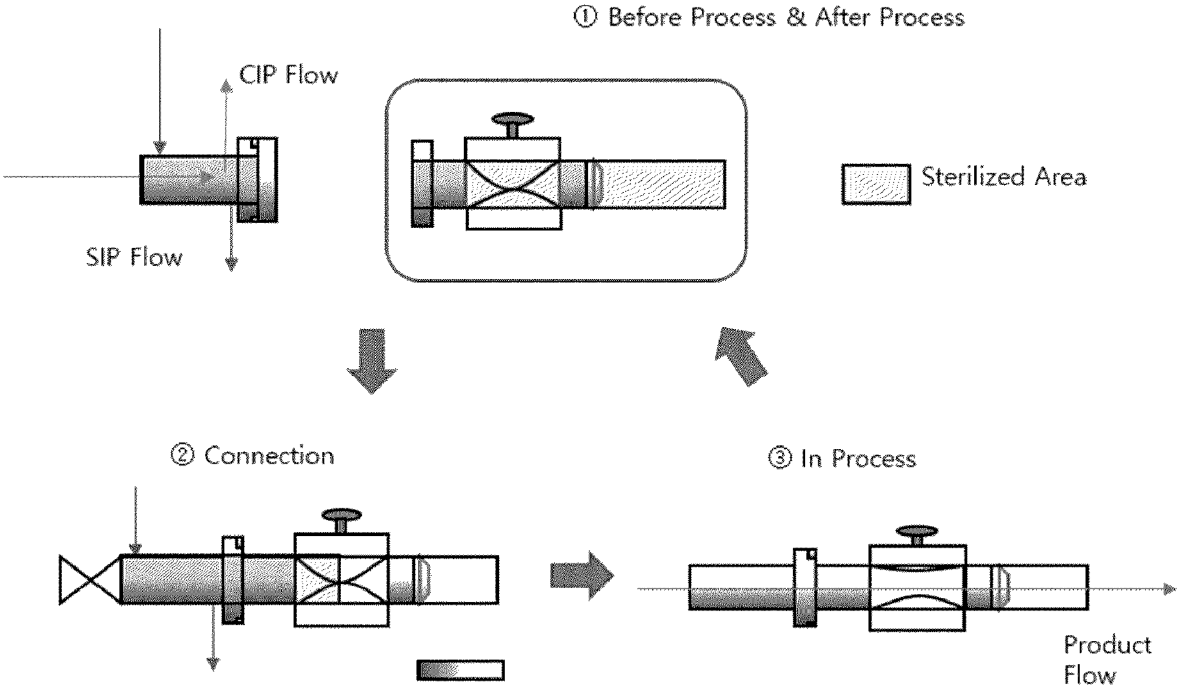
FIG. 3 is a schematic diagram showing the operation of a diaphragm valve in a fastening part of an aseptic connection system according to one embodiment of the present invention.

Meanwhile, the fastening part may be included to effectively connect the discharge line made of a stainless steel material and an SU disposable tube, and may include, if needed, one or more components selected from a flange, tri-clamp, a cap and diaphragm valves. Among these, the flange may be a component that controls opening/closing through rotation, the tri-clamp is a component for fastening, the cap is a component for hermetically sealing a tube, and the diaphragm valve is a component included to control line opening/closing and a flow rate (see FIGS. 2 and 3).

Meanwhile, the vent filter is a component for preventing the expansion and contraction of a tube by a steam sterilization process, and may be, for example, a capsule vent filter having a pore size of 0.2 μm. The steam trap tube may be included to easily discharge steam condensate, and the pinch clamp may be removed after sterilization.

In further detail, the discharge line and the SU disposable tube are inclined to form an acute angle based on the ground, and are connected to each other in a "V" shape through the fastening part, and moreover, when a steam trap tube branched from the fastening part and including a pinch clamp is further included, the discharge line and the SU disposable tube are formed in a "Y" shape.

As described above, when the discharge line and the SU disposable tube are inclined to form an acute angle based on the ground, due to sliding caused by gravity and the predetermined angle, the fluid flowability in the medium transfer line is improved compared to the conventional T-shaped general configuration, thereby preventing impurities such as a condensate from remaining in the medium transfer line that includes the discharge line and/or the SU disposable tube, so medium contamination is prevented in advance.

Meanwhile, the SU disposable tube according to one embodiment of the present invention may be formed by connecting a tube previously connected with the fastening part with a tube included in the bioreactor through a welding process.

For example, when both of the medium storage tank and the bioreactor are SS process systems formed of an SS material, although there is no complicated piping, they are vulnerable to contamination and have poor process flexibility, and when both of the medium storage tank and the bioreactor are SU process systems formed of an SU material, although they are resistant to contamination, complicated piping and scale-up are difficult and there is a high operation cost.

On the other hand, in the case of the hybrid system employing the medium storage tank made of an SS material and the bioreactor made of an SU disposable bag according to one embodiment of the present invention, although the aforementioned advantages of the SS process system and the SU process system may be obtained at the same time, in the process of replacing the bioreactor made of the SU disposable bag, there is a problem in that a line opening inevitably occurs.

On the other hand, according to the present invention, in the process of replacing the bioreactor made of the SU disposable bag, following the sterilization process, joining between the SU disposable tubes is made through a welding process, so joining with completely ensured sterility is possible and thus medium contamination caused by a line opening can be perfectly prevented.

Meanwhile, the welding process may be performed using a welder, and may be performed with a general method and conditions used in the art, but the present invention is not particularly limited thereto.

Meanwhile, the aseptic connection system according to one embodiment of the present invention may be applied to provide a medium for a process of manufacturing one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b, and it can be variously used throughout a process of manufacturing antibody pharmaceuticals, such as biopharmaceuticals, improved biopharmaceuticals (biobetters) and biosimilars.

Aseptic Connection Method in Hybrid System for Process of Manufacturing Antibody Pharmaceutical Meanwhile, according to one embodiment of the present invention, an aseptic connection method in the system may include (a) after transferring a medium from a medium storage tank to a bioreactor, removing an SU disposable tube that has been used; (b) connecting a new disposable tube to a fastening part first, cleaning the medium storage tank, the discharge line and the disposable tube in place, drying the resulting product using clean and oil-free air (COA), and then sterilizing the dried product with high-temperature steam; and (c) aseptically connecting, after the sterilization, the disposable tube with a tube included in a newly-prepared bioreactor made of a single-use (SU) disposable bag through a welding process.

In addition, according to another embodiment of the present invention, an aseptic connection method in the system may include (a) after transferring a medium from a medium storage tank to a bioreactor, removing an SU disposable tube that has been used; (b) preparing a new disposable tube having a diaphragm valve at one end and a vent filter at the other end, cleaning the tube in place, drying it using clean and oil-free air (COA) and then sterilizing it with high temperature steam; and (c) connecting, after the sterilization, the end at which the diaphragm valve of the disposable tube is placed with a discharge line of a medium storage tank via a fastening part, and aseptically connecting the end at which the vent filter is included with a tube included in a newly prepared bioreactor made of an SU disposable bag through a welding process.

Meanwhile, for connection with completely secured sterility, in (c), sterilizing the fastening part after connecting an end of the region where the diaphragm valve is placed with the discharge line of the medium storage tank via the fastening part may be further included.

According to the aseptic connection system and aseptic connection method of the present invention as described above, in the hybrid system employing the medium storage tank made of an SS material and the bioreactor made of the SU disposable bag, by interconnection of the SU disposable tube through a welding process, a completely aseptic connection between the medium storage tank and the bioreactor may be secured, and the advantages of both the SS system and the SU system may be obtained at the same time.

In addition, in the aseptic connection system according to the present invention, by forming the discharge line, the SU disposable tube and the steam trap tube in a "Y" shape, the flowability in a medium transfer line can be improved, thereby preventing impurities such as a condensate from remaining in the medium transfer line and thus preventing medium contamination in advance.

Further, the aseptic connection system and aseptic connection method according to the present invention may exclude complicated piping caused by the single use of a conventional SU system, and due to the advantages of resistance to contamination compared to the single use of a conventional SS system, may secure the economic feasibility and efficiency of the process.

In the above, the present invention has been described with reference to exemplary embodiments, but the present invention is not limited to the described embodiments, and it is obvious to those skilled in the art or those of ordinary skill in the art that the present invention can be variously modified and changed without departing the spirit and scope of the present invention. Accordingly, such modifications or variations should not be individually understood from the technical spirit or point of view of the present invention, and the modified embodiments should belong to the claims of the present invention.

What is claimed is:

1. A hybrid aseptic connection system for a process of manufacturing an antibody pharmaceutical, comprising:

a medium storage tank made of a stainless steel material, which stores a medium received from a media preparation tank; a bioreactor made of a single-use (SU) disposable bag, which includes a stirrer, receives the medium from the medium storage tank and increases the number of cells through cell division; and a medium transfer line configured to introduce a medium stream discharged from the medium storage tank to the bioreactor, wherein the medium transfer line includes a fastening part formed at the end of a discharge line provided at one end of the medium storage tank; an SU disposable tube connected with the discharge line using the fastening part at one end and connected with the bioreactor at the other end; wherein the discharge line connected to the medium storage tank and the SU disposable tube connected to the bioreactor are connected with each other while being inclined at predetermined angles, respectively, and a vent filter provided on the tube to prevent the expansion and contraction of the tube by a steam sterilization process, wherein the discharge line, the SU disposable tube and a steam trap tube are formed in an "Y" shape, wherein the steam trap tube forms a lower branch of the "Y" shape and is branched from the fastening part, includes a pinch clamp, and is configured to discharge steam condensate, wherein the steam trap tube is further configured to discharge steam condensate remaining in the medium transfer line through the lower branch of the "Y" shape by gravity; and wherein the steam trap tube is a part of a single use tube and the discharge line is made of a stainless steel material.

2. The system of claim 1, wherein the SU disposable tube is formed by welding a tube pre-connected with the fastening part and a tube included in the bioreactor.

3. The system of claim 1, wherein the aseptic connection system is applied to provide a medium for a process of manufacturing one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b.

* * * * *